United States Patent [19]

Groth, Jr. et al.

[11] 4,069,518
[45] Jan. 24, 1978

[54] TOTAL ANKLE PROSTHESIS

[76] Inventors: Harry E. Groth, Jr., 3840 SW. Dosch Road, Portland, Oreg. 97201; Philip J. Fagan, 3480 SW. 106th St., Beaverton, Oreg. 97005

[21] Appl. No.: 719,228

[22] Filed: Aug. 31, 1976

[51] Int. Cl.² .............................................. A61F 1/24
[52] U.S. Cl. .................................... 3/1.91; 128/92 C
[58] Field of Search .................. 3/1.91, 1.9, 1, 1.911, 3/1.912; 128/92 C

[56] References Cited

U.S. PATENT DOCUMENTS

| 3,872,519 | 3/1975 | Giannestras et al. | 3/1.91 |
| 3,896,502 | 7/1975 | Lennox | 3/1.91 |

Primary Examiner—Ronald L. Frinks
Attorney, Agent, or Firm—Richard H. Brink; David J. Mugford

[57] ABSTRACT

A prosthetic joint for the replacement of the ankle joint comprising a tibial member and a talar member each having three distinct complementary bearing surfaces which allow plantar and dorsal flexion and some rotation approximating the movement of the natural ankle joint. The talar member has three adjacent bearing surfaces which are each longitudinally and laterally convexly shaped and the tibial member is provided with three substantially complementary longitudinally and laterally concavely shaped bearing surfaces that provide medial-lateral support while allowing about 5° rotation between the members.

8 Claims, 8 Drawing Figures

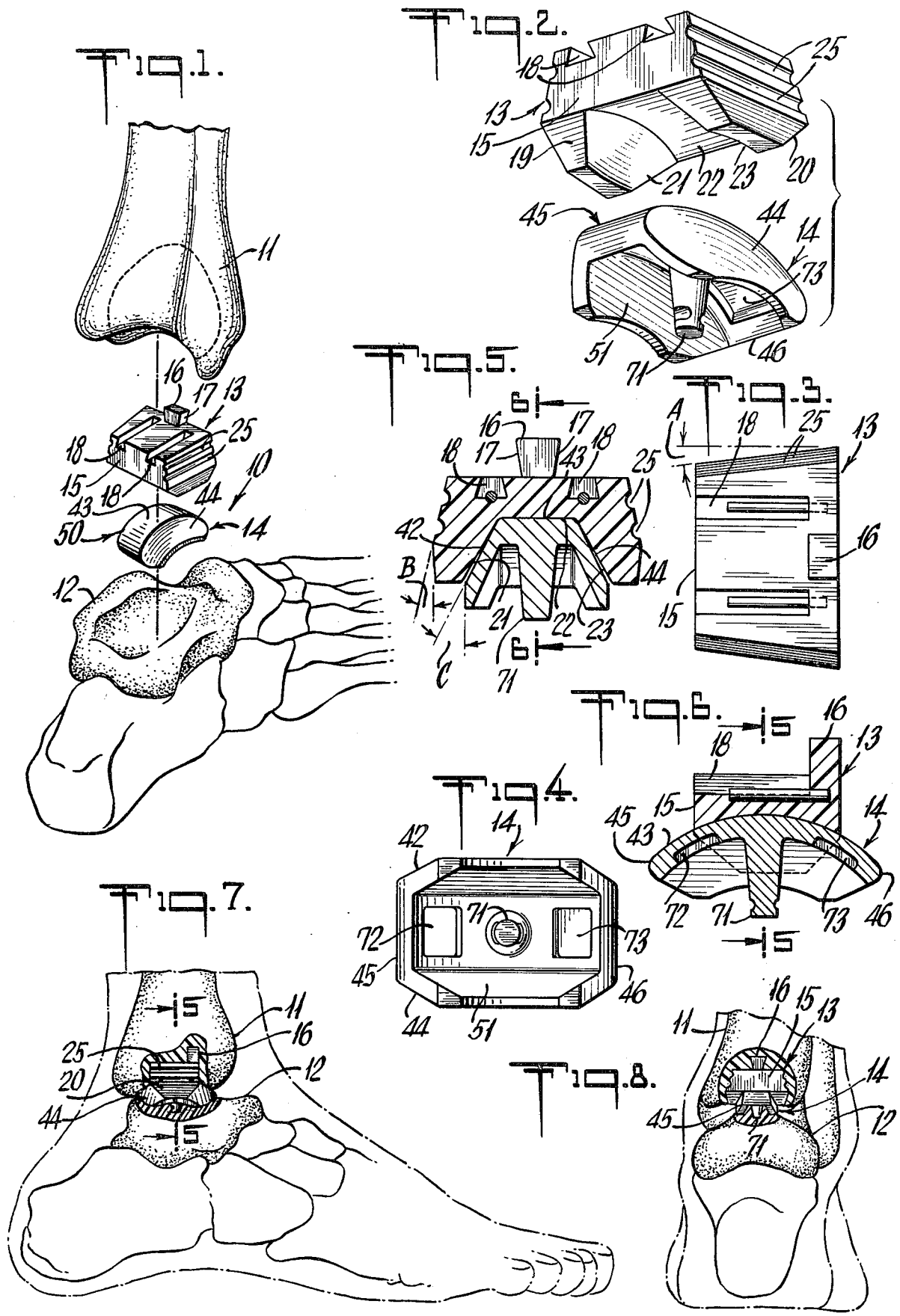

TOTAL ANKLE PROSTHESIS

BACKGROUND OF THE INVENTION

This invention relates to a prosthetic ankle joint, and more particularly to a prosthetic joint for replacement of the ankle joint. The prosthetic joint is adapted to be implanted in the body of human beings.

Heretofore, prosthetic joints have been used to replace defective natural joints in humans when such joints have become diseased such as the result of arthritis or injured through accident. However, prior art prosthetic members have not been wholly satisfactory for ankle implantation. They have suffered from various deficiencies including being difficult to implant and not having sufficient range of motion, some have the problem of tending to dislocate easily resulting in extreme pain to the individual and in some case requiring a surgical procedure to bring the components of the prosthesis into proper alignment. Other prostheses have produced painful irritation to the surfaces of the ankle and have produced an unstable prosthetic joint.

Accordingly, it is an object of this invention to provide a new and improved joint prosthesis for total ankle replacement which provides articulation similar to that of the natural joint and one that overcomes the deficiencies described above.

SUMMARY OF THE INVENTION

In accordance with the present invention, an ankle prosthesis comprising a tibial member and a talar member is provided, the tibial member having three distinct adjacent concave articular surfaces and the talar member having three convex articular surfaces closely approximating the tibial surfaces. The width of the central surface of the tibial component is slightly wider than the corresponding surface fo the talar component to allow approximately 5° of rotation. The lateral surfaces of the tibial component cover approximately 70% of the corresponding surfaces of the talar component. The tibial member and the talar member have means for attachment to the tibia and talus respectively producing a stable joint with motion approximating that of the natural ankle joint.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring now to the drawings which form a part of this original disclosure:

FIG. 1 is an exploded, perspective view illustrating the relationship of the ankle prosthesis relative to the tibia and talus;

FIG. 2 is a perspective view of the prosthesis;

FIG. 3 is a top plan view of the tibial member of the prosthesis;

FIG. 4 is a bottom plan view of the talar member of the prosthesis;

FIG. 5 is a sectional view of the prosthesis taken along lines 5—5 of FIG. 6;

FIG. 6 is a sectional view of the prosthesis taken along lines 6—6 of FIG. 5;

FIG. 7 is a lateral view, partly in section of a foot showing the relationship of the tibial and talar members of the prosthesis; and FIG. 8 is a view, partly in section from the back of the heel as seen from the left side of the foot of FIG. 7.

DESCRIPTION OF THE PREFERRED EMBODIMENT

Referring to the drawings in further detail as shown in FIGS. 1–6 and 7–8, there is seen an ankle joint prosthesis which is constructed in accordance with the principles of this invention and designated generally by reference number 10. In FIG. 1 the prosthesis is shown in relation to its connection to the distal tibia 11 and the talar crown 12, respectively. The prosthetic joint 10 is formed by a tibial member 13 inserted into the tibia and a talar member 14 inserted into the talus. The distal end of the tibia, and the crown of the talus are prepared with a minimum of bone removal by cutting and/or reaming the end portions so that the prosthetic members 13 and 14 can be affixed to the corresponding bones.

The tibial member may be fabricated from biologically compatible material such as high density polyethylene high or ultra-high molecular weight polyethylene. The tibial member consists of a generally trapezoidal-shaped body 15. Integrally joined to and extending upwardly from approximately the center of the forward edge of the block is a lug 16 having tapered sides 17 converging toward block 15. The upper surface of the block contains dove-tailed tracks 18 in the anterior/posterior direction. The tracks and lug are designed for cement fixation. The lower surface of the block and sidewalls 19 and 20 define three distinct concavely curved both longitudinally and laterally bearing surfaces 21, 22 and 23. The external surfaces 19 and 20 of the tibial member are tapered. The width of the superior external surface decreases posteriorly the angle A being 1° to 40° and preferably about 5° and conforms to the trapezoidal cross-section of the distal tibia and provides a good fit in bone. The width of the tibial member increases inferiorly which corresponds to angle B, preferably 10°.

Grooves 25 are located in the external surface of side walls to allow bone cement fixation. The grooves are parallel in the anterior/posterior direction.

The three concave articular surfaces 21, 22 and 23 of the tibial component match the three talar articular surfaces quite closely. The width of the central surface of the tibial component is slightly wider about 0.015 inches than the corresponding surface in the talar component. This difference allows for approximately 5° of rotation. The lateral surfaces of the tibial component cover approximately 70% of the corresponding surfaces of the talar component.

The talar member 14 may be fabricated from a biologically compatible metal or metal alloy consisting of cobalt, chromium and molybdenum and includes an upper portion 50 and lower attachment portion 51 wherein the upper portion is provided with bearing surfaces 42, 43 and 44 which are complementary to bearing surfaces 21, 22 and 23 of the tibial member 3. The bearing surfaces 42, 43 and 44 are longitudinally and laterally convex. The length of the central or upper bearing surface 43 of the talar member when viewed from its medial side as seen in FIG. 8 is generally longitudinally and laterally convex and the lateral bearing surfaces 42 and 44 are also longitudinally and laterally convex and are inclined at and angle C from 5°–70° and preferably from 25° -70°, and more preferably 30° from the vertical.

The anterior and posterior edges 45 and 46 of the talar member 14 are blunt to prevent scraping of the bone or soft tissue anterior or posterior to the metal prosthesis. Located on the underside of the central surface of the talar member is a short post 71 for cement fixation in bone. This post is located centrally and in addition two rectangular depressions 72 and 73 are located anteriorly and posteriorly to this post. These depressions allow bone cement to "key" in the prosthesis. All three bearing surfaces are load bearing and also the lateral surfaces limit lateral and medial movement of the talar component thereby providing medial-lateral stability.

In use the tibial component articulates on the talar component and provides for plantar and dorsal flexion. The anterior/posterior length of the tibial component is shorter than the talar component. This allows the tibial component to ride anteriorly and posteriorly over the talar component. The range of motion provided by this prosthesis is about 40°. A limited amount of rotation is permitted by the clearance created between the central articular surfaces of the tibial and talar component.

In practice, the surgical procedure preferably involves cutting out a section of the anterior tibia and cutting a notch in the central part of the tibia to accommodate lug 16. Through the use of a template and drill a bore to accommodate post 71 is provided in the crown of the talus and the crown is tailored to accommodate the talal component. Cement, e.g., methyl methacrylate cement is then applied to the site and the lug and post entered into their corresponding bone notches and bore.

While various advantageous embodiments have been chosen to illustrate the invention, it will be understood by those skilled in the art that various changes and modifications can be made therein without departing from the scope of the invention as defined in the appended claims.

We claim:

1. An ankle prosthesis comprising a talar member having three adjacent longitudinally and laterally convexly shaped bearing surfaces and means for attaching said member to the talus bone and a tibial member having three substantially complementary longitudinally and laterally concave shaped bearing surfaces and means for attaching said member to the talus bone; wherein said convex surfaces and said concave surfaces are in mutual articulatory bearing engagement and provide medial-lateral support.

2. A prosthesis according to claim 1 wherein the bearing surfaces of the talar member and the tibial member each consist of a central surface and lateral surfaces adjacent said central surface.

3. The prosthesis according to claim 2 wherein the lateral bearing surfaces are oriented from about 25°-70° from the vertical.

4. The prosthesis according to claim 3 wherein the lateral bearing surfaces are oriented about 30° from the vertical.

5. The prosthesis according to claim 4 wherein the difference in width between the central bearing surface of the tibial component and the central bearing surface of the talar component is sufficient to allow about 5° rotation of the talar component with respect to the tibial component.

6. The prosthesis according to claim 5 wherein the tibial component exterior width is greater in the anterior than in the posterior.

7. The prosthesis according to claim 6 wherein said means for attaching the talar member to the talus comprises a post and the means for attaching the tibial member to the tibia comprises a lug both said post and said lug extending substantially perpendicular from the surface opposite the central bearing surface of the respective talar member and tibial member.

8. The prosthesis according to claim 7 wherein said means for attaching the tibial member further comprises two parallel tracks.

* * * * *